United States Patent
Drysdale et al.

(10) Patent No.: US 8,487,095 B2
(45) Date of Patent: Jul. 16, 2013

(54) ACID ADDITION SALTS, HYDRATES AND POLYMORPHS OF 5-(2,4-DIHYDROXY-5-ISO-PROPYL-PHENYL)-4-(4-MORPHOLIN-4-YLMETHYL-PHENYL)-ISOXAZOLE-3-CARBOXYLIC ACID ETHYLAMIDE AND FORMULATIONS COMPRISING THESE FORMS

(75) Inventors: Martin James Drysdale, Berkshire (GB); Brian William Dymock, Singapore (SG); Christoph Krell, Basel (CH); Michael Mutz, Freiburg (DE); Holger Petersen, Eimeldingen (DE); Weijia Zheng, Cambridge, MA (US)

(73) Assignees: Novartis AG, Basel (CH); Vernalis (R&D) Ltd

( * ) Notice: Subject to any disclaimer, the term of this patent is extended or adjusted under 35 U.S.C. 154(b) by 0 days.

(21) Appl. No.: 13/415,268

(22) Filed: Mar. 8, 2012

(65) Prior Publication Data

US 2012/0172592 A1 Jul. 5, 2012

Related U.S. Application Data

(62) Division of application No. 12/529,090, filed as application No. PCT/EP2008/052443 on Feb. 28, 2008, now Pat. No. 8,163,747.

(30) Foreign Application Priority Data

Mar. 1, 2007 (EP) .................................... 07103346

(51) Int. Cl.
*C07D 413/10* (2006.01)

(52) U.S. Cl.
USPC ........................................................ 544/137

(58) Field of Classification Search
USPC ........................................................ 544/137
See application file for complete search history.

(56) References Cited

U.S. PATENT DOCUMENTS

2006/0070405 A1  4/2006  Jones et al.

FOREIGN PATENT DOCUMENTS

| CL | 470/2008 | 2/2008 |
|---|---|---|
| WO | WO2004/072051 | 8/2004 |
| WO | WO 2010/069458 | 6/2010 |

OTHER PUBLICATIONS

Morissette, Sherry, et al: "High-throughput crystallization: polymorphs, salts, co-crystals and soicates of pharmaceutical solids", Advanced Drug Delivery Reviews, Amsterdam, NL: 2004, vol. 56, No. 3, pp. 275-300.
Caira, M.R.: "Crystalline polymorphism of organic compounds", Topics in Current Chemistry, Springer, Berlin, DE, 1998, vol. 198, pp. 163-208.
Gould, P.L.: "Salt selection for basic drugs", International Journal of Pharmaceutics, Amsterdam, NL; 1986, vol. 33, No. 1/3, pp. 201-217.
Tong, W.Q., et al: "In situ salt screening—a useful technique for discovery support and preformulation studies", May 1998; vol. 3, No. 2, pp. 215-233.
Bastin et al., 2000, "Salt Selection and Optimisation Procedures for Pharmaceutical New Chemical Entities", Organic Process Research & Development, 4:427-435.
Andersen et al."Preparation of Water-Soluble Compounds Through Salt Formation", The Practice of Medicinal Chemistry, pp. 739-746, 1996.
Dr. Sofia Papathoma, 2006, Patenting polymorphs at the European Patent Office.

*Primary Examiner* — Rebecca Anderson
(74) *Attorney, Agent, or Firm* — Cozette McAvoy

(57) ABSTRACT

The present invention relates to new salt forms of 5-(2,4-dihydroxy-5-isopropyl-phenyl)-4-(4-morpholin-4-ylmethyl-phenyl)-isoxazole-3-carboxylic acid ethylamide, in particular the mesylate, hydrochloride, tartrate, phosphate and hemi fumarate salt thereof; to crystalline forms of such salts; to polymorphs of 5-(2,4-dihydroxy-5-isopropyl-phenyl)-4-(4-morpholin-4-ylmethyl-phenyl)-isoxazole-3-carboxylic acid ethylamide; to hydrates and polymorphs of the new salt forms mentioned above; to the use of the new salt forms mentioned above for the manufacture of a medicament for the treatment of a disorder mediated by Hsp90; to a method for treating a disorder mediated by Hsp90 using the new salt forms; to formulations comprising such salt forms, in particular aqueous solutions suitable for intravenous administration; and to amber glass containers being filled with such formulations.

3 Claims, 13 Drawing Sheets

ACID ADDITION SALTS, HYDRATES AND POLYMORPHS OF 5-(2,4-DIHYDROXY-5-ISO-PROPYL-PHENYL)-4-(4-MORPHOLIN-4-YLMETHYL-PHENYL)-ISOXAZOLE-3-CARBOXYLIC ACID ETHYLAMIDE AND FORMULATIONS COMPRISING THESE FORMS

This is a divisional of application Ser. No. 12/529,090 filed on Aug. 28, 2009, U.S. Pat. No. 8,163,747 which is a National Stage of International Application No. PCT/EP2008/052443 filed on Feb. 28, 2008, which claims priority under 35 U.S.C. §119 to European Patent Application Serial No. 07103346.8 filed Mar. 1, 2007 which in its entirety are herein incorporated by reference.

The present invention relates to new salt forms and polymorphs of 5-(2,4-dihydroxy-5-isopropyl-phenyl)-4-(4-morpholin-4-ylmethyl-phenyl)-isoxazole-3-carboxylic acid ethylamide, to hydrates and polymorphs of such new salt forms and to new formulations comprising such salt forms.

The Hsp90 family of chaperones is comprised of four known members: Hsp90α and Hsp90β both in the cytosol, grp94 in the endoplasmic reticulum and trap-1 in the mitochondria. Hsp90 is an abundant cellular chaperone required for the ATP-dependent refolding of denatured or "unfolded" proteins and for the conformational maturation of a variety of key proteins involved in the growth response of the cell to extracellular factors. These proteins, which are called client proteins, include the steroid receptors as well as various protein kinases. Hsp90 is essential for eukaryotic cell survival and is overexpressed in many tumors. Cancer cells seem to be sensitive to transient inhibition of Hsp90 ATPase activity suggesting that Hsp90 inhibitors could have a potential as new anticancer drugs. Each Hsp90 family member possesses a conserved ATP-binding site at its N-terminal domain, which is found in few other ATP-binding proteins. The weak ATPase activity of Hsp90 is stimulated upon its interaction with various co-chaperone proteins. Several natural compounds such as geldanamycin or radicicol bind at the ATP-binding site of Hsp90 inhibiting its ATPase activity. In cellular systems and in vivo, these drugs upon binding to Hsp90 prevent the folding of the client proteins, which are then degraded in the proteasome. 17-allylamino-17-demethoxy-geldanamycin (17-AAG), a geldanamycin derivative, is tested in Phase I clinical trials. Initial clinical experiences with 17-AAG have offered preliminary evidence that concentrations of the drug associated with activity in pre-clinical systems can be achieved in humans with tolerable toxicity, and provided early evidence of target modulation in at least certain surrogate and tumor compartments. The dose limiting toxicity of 17-AAG is hepatic toxicity. 17-AAG's poor solubility makes it difficult to formulate/administer and its synthesis is difficult (it is generally obtained by fermentation). Therefore alternative compounds with better physicochemical properties and maybe of higher specificity (17-AAG inhibits all these the four Hsp90 paralogs) are needed. WO 2004/072051 discloses such alternative compounds, more specifically a series of isoxazoles derivatives with inhibition properties for heat shock proteins.

5-(2,4-Dihydroxy-5-isopropyl-phenyl)-4-(4-morpholin-4-ylmethyl-phenyl)-isoxazole-3-carboxylic acid ethylamide is a Hsp90 inhibitors described in WO 2004/072051 (Example 78). The compound can be prepared, for instance, as disclosed in such publication. 5-(2,4-Dihydroxy-5-isopropyl-phenyl)-4-(4-morpholin-4-ylmethyl-phenyl)-isoxazole-3-carboxylic acid ethylamide is a poorly water soluble compound, which shows a solubility in water of less than 0.1 mg/ml. The solubility of the free base in 0.1 N HCl is about 1-2.5 mg/ml. Furthermore, the free base is slightly hygroscopic showing a maximum uptake of 1.8% of water at 80% relative humidity (r.h.) at 25° C.

Surprisingly, new salt forms of 5-(2,4-dihydroxy-5-isopropyl-phenyl)-4-(4-morpholin-4-ylmethyl-phenyl)-isoxazole-3-carboxylic acid ethylamide were found including the hydrochloride, tartrate, phosphate, hemi fumarate and the mesylate salt. These salts and the free base were found to be crystalline rendering these forms particularly suitable for pharmaceutical development.

Neither of 5-(2,4-dihydroxy-5-isopropyl-phenyl)-4-(4-morpholin-4-ylmethyl-phenyl)-isoxazole-3-carboxylic acid ethylamide mesylate and 5-(2,4-dihydroxy-5-isopropyl-phenyl)-4-(4-morpholin-4-ylmethyl-phenyl)-isoxazole-3-carboxylic acid ethylamide hydrochloride was found to be hygroscopic.

Furthermore, it was found that 5-(2,4-dihydroxy-5-isopropyl-phenyl)-4-(4-morpholin-4-ylmethyl-phenyl)-isoxazole-3-carboxylic acid ethylamide mesylate is superior compared to the free base as well as other salts in terms of solubility. Besides the advantage of exhibiting a high water solubility, the mesylate salt is also suitable to be manufactured reproducibly in a clear acid/base ratio. This finding renders the mesylate salt particularly suitable for the use in liquid formulations for oral as well as for intravenous formulations.

All of 5-(2,4-dihydroxy-5-isopropyl-phenyl)-4-(4-morpholin-4-ylmethyl-phenyl)-isoxazole-3-carboxylic acid ethylamide salts show higher solubility compared with free base.

The solubility of the hydrochloride salt in water is 2.5-5 mg/ml, at pH 5 it is approximately 1-2.5 mg/ml and is less than 1 mg/ml in 0.1 N HCl.

The solubility of the tartrate salt in water is more than 2 mg/ml.

The solubility of the phosphate salt in water is approximately 0.5-1.0 mg/ml.

The solubility of the hemi fumarate salt in water is approximately 0.1-0.25 mg/ml.

The solubility of the mesylate salt at pH 5 is approximately 1-2.5 mg/ml and 10-20 mg/ml in 0.1 N HCl. The solubility in water at pH 4 was found to be 33.5 mg/ml.

In addition to the above, it has been found that 5-(2,4-dihydroxy-5-isopropyl-phenyl)-4-(4-morpholin-4-ylmethyl-phenyl)-isoxazole-3-carboxylic acid ethylamide mesylate can be obtained in the form of hydrates. Modification A is an anhydrous form of 5-(2,4-dihydroxy-5-isopropyl-phenyl)-4-(4-morpholin-4-ylmethyl-phenyl)-isoxazole-3-carboxylic acid ethylamide mesylate and forms $H_A$ and $H_B$ are hydrated forms of 5-(2,4-dihydroxy-5-isopropyl-phenyl)-4-(4-morpholin-4-ylmethyl-phenyl)-isoxazole-3-carboxylic acid ethylamide mesylate.

As a further aspect of the present invention, it has been found that different crystalline forms of the free base and of the mesylate salt of 5-(2,4-dihydroxy-5-isopropyl-phenyl)-4-(4-morpholin-4-ylmethyl-phenyl)-isoxazole-3-carboxylic acid ethylamide can be obtained.

Finally, it was found that the crystalline form 5-(2,4-dihydroxy-5-isopropyl-phenyl)-4-(4-morpholin-4-ylmethyl-phenyl)-isoxazole-3-carboxylic acid ethylamide hydrochloride did not change by equilibration in suspension over a range of applied conditions. Lack of polymorphism is a beneficial property for a solid form designated to be developed as a medicament.

Hence, in a first aspect, the present invention relates to new salts of 5-(2,4-dihydroxy-5-isopropyl-phenyl)-4-(4-morpholin-4-ylmethyl-phenyl)-isoxazole-3-carboxylic acid ethylamide, more specifically to 5-(2,4-dihydroxy-5-isopropyl-phenyl)-4-(4-morpholin-4-ylmethyl-phenyl)-isoxazole-3-carboxylic acid ethylamide mesylate, 5-(2,4-dihydroxy-5-isopropyl-phenyl)-4-(4-morpholin-4-ylmethyl-phenyl)-isoxazole-3-carboxylic acid ethylamide hydrochloride, 5-(2,4-dihydroxy-5-isopropyl-phenyl)-4-(4-morpholin-4-ylmethyl-phenyl)-isoxazole-3-carboxylic acid ethylamide tartrate, 5-(2,4-dihydroxy-5-isopropyl-phenyl)-4-(4-morpholin-4-ylmethyl-phenyl)-isoxazole-3-carboxylic acid ethylamide phosphate and 5-(2,4-dihydroxy-5-isopropyl-phenyl)-4-(4-morpholin-4-ylmethyl-phenyl)-isoxazole-3-carboxylic acid ethylamide hemi fumarate.

In a second aspect, the present invention relates to new crystalline forms and hydrates of 5-(2,4-dihydroxy-5-isopropyl-phenyl)-4-(4-morpholin-4-ylmethyl-phenyl)-isoxazole-3-carboxylic acid ethylamide mesylate.

In a third aspect, the present invention relates to new crystalline forms of 5-(2,4-dihydroxy-5-isopropyl-phenyl)-4-(4-morpholin-4-ylmethyl-phenyl)-isoxazole-3-carboxylic acid ethylamide free base.

Additionally, the present invention relates to the use of 5-(2,4-dihydroxy-5-isopropyl-phenyl)-4-(4-morpholin-4-ylmethyl-phenyl)-isoxazole-3-carboxylic acid ethylamide mesylate, 5-(2,4-dihydroxy-5-isopropyl-phenyl)-4-(4-morpholin-4-ylmethyl-phenyl)-isoxazole-3-carboxylic acid ethylamide hydrochloride, 5-(2,4-dihydroxy-5-isopropyl-phenyl)-4-(4-morpholin-4-ylmethyl-phenyl)-isoxazole-3-carboxylic acid ethylamide tartrate, 5-(2,4-dihydroxy-5-isopropyl-phenyl)-4-(4-morpholin-4-ylmethyl-phenyl)-isoxazole-3-carboxylic acid ethylamide phosphate and 5-(2,4-dihydroxy-5-isopropyl-phenyl)-4-(4-morpholin-4-ylmethyl-phenyl)-isoxazole-3-carboxylic acid ethylamide hemi fumarate for the manufacture of a medicament for the treatment of a disorder mediated by Hsp90.

The general terms used hereinbefore and hereinafter preferably have within the context of this disclosure the following meanings, unless otherwise indicated.

The expression "disorders mediated by Hsp90" as used herein denotes disorders, such as tumor diseases, which result from overexpression, activation or dysregulation of Hsp90 or wherein such overexpression, activation or dysregulation play a prominent role.

The expression "free of any other salts" as used herein means that neither any salts derived from inorganic or organic acids, such as sodium chloride, as isotonic agent nor any buffer salts are present. It was observed that in the presence of such other salts crystals are formed sooner or later, which renders the solution of 5-(2,4-dihydroxy-5-isopropyl-phenyl)-4-(4-morpholin-4-ylmethyl-phenyl)-isoxazole-3-carboxylic acid ethylamide mesylate unstable and which is in particular an unacceptable risk for a formulation designated to be used for intravenous administration.

The expression "chemically stable" as used herein means that 5-(2,4-dihydroxy-5-isopropyl-phenyl)-4-(4-morpholin-4-ylmethyl-phenyl)-isoxazole-3-carboxylic acid ethylamide does not undergo any chemical reactions, such as solvolysis, especially no hydrolysis, rearrangements or oxidations.

SHORT DESCRIPTION OF THE FIGURES

FIGS. 1 to 13 X-ray diffraction diagrams of crystalline forms of the free base, the methane sulphonic acid salt, the hydrochloric salt, the tartic acid salt, the phosphoric acid salt and the hemi fumaric acid salt of 5-(2,4-dihydroxy-5-isopropyl-phenyl)-4-(4-morpholin-4-ylmethyl-phenyl)-isoxazole-3-carboxylic acid ethylamide. In the X-ray diagrams, the angle of refraction 2theta are plotted on the horizontal axis (x-axis) and the relative line intensity (background-corrected peak intensity) on the vertical (y-axis). X-ray powder diffraction patterns are measured with Cu Kα radiation source (Kα1 radiation, wavelength λ=1.54060 Angström).

Figure 1:
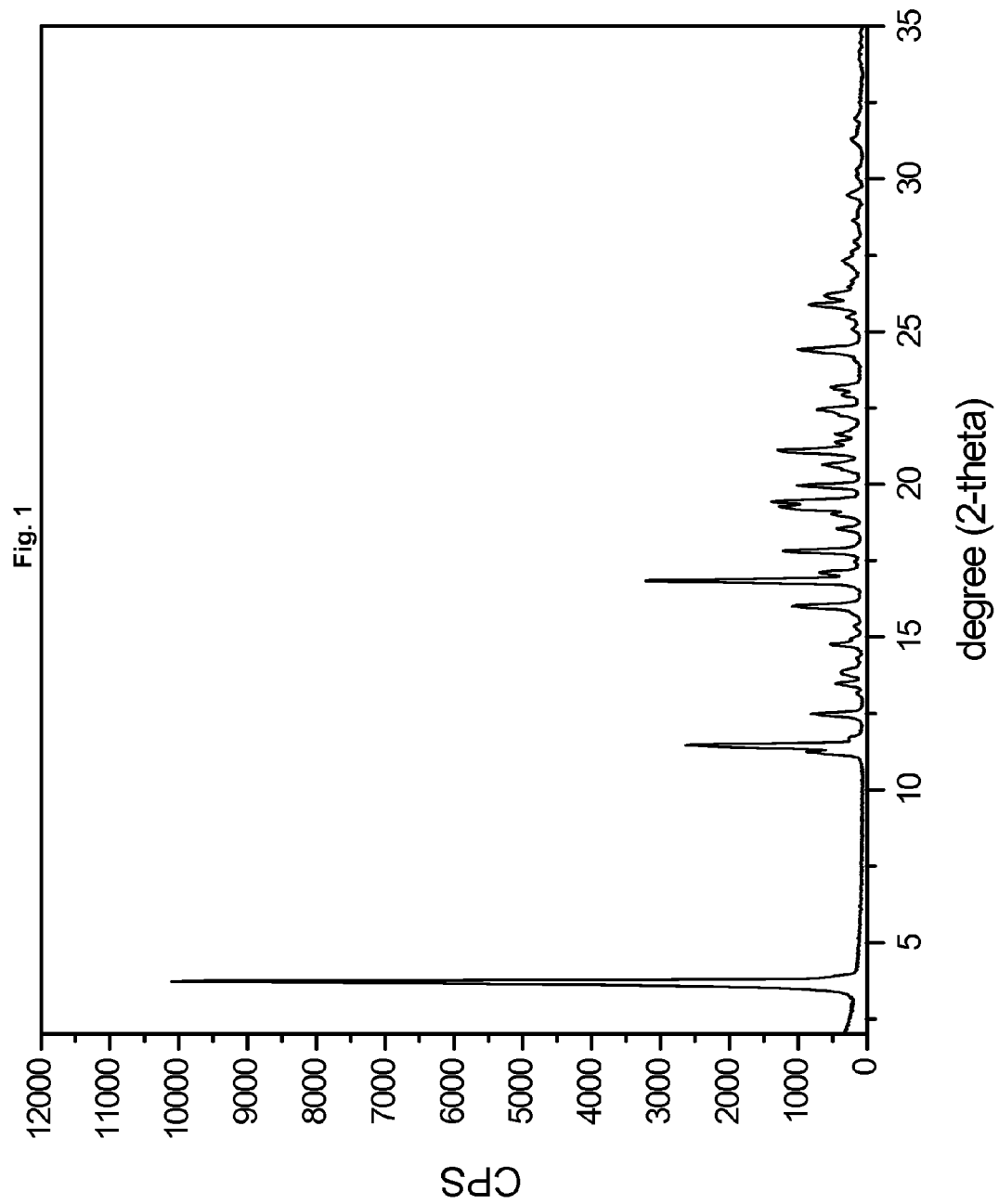
FIG. 1 shows the X-ray diffraction diagram of 5-(2,4-dihydroxy-5-isopropyl-phenyl)-4-(4-morpholin-4-ylmethyl-phenyl)-isoxazole-3-carboxylic acid ethylamide free base, form I.
Figure 2:
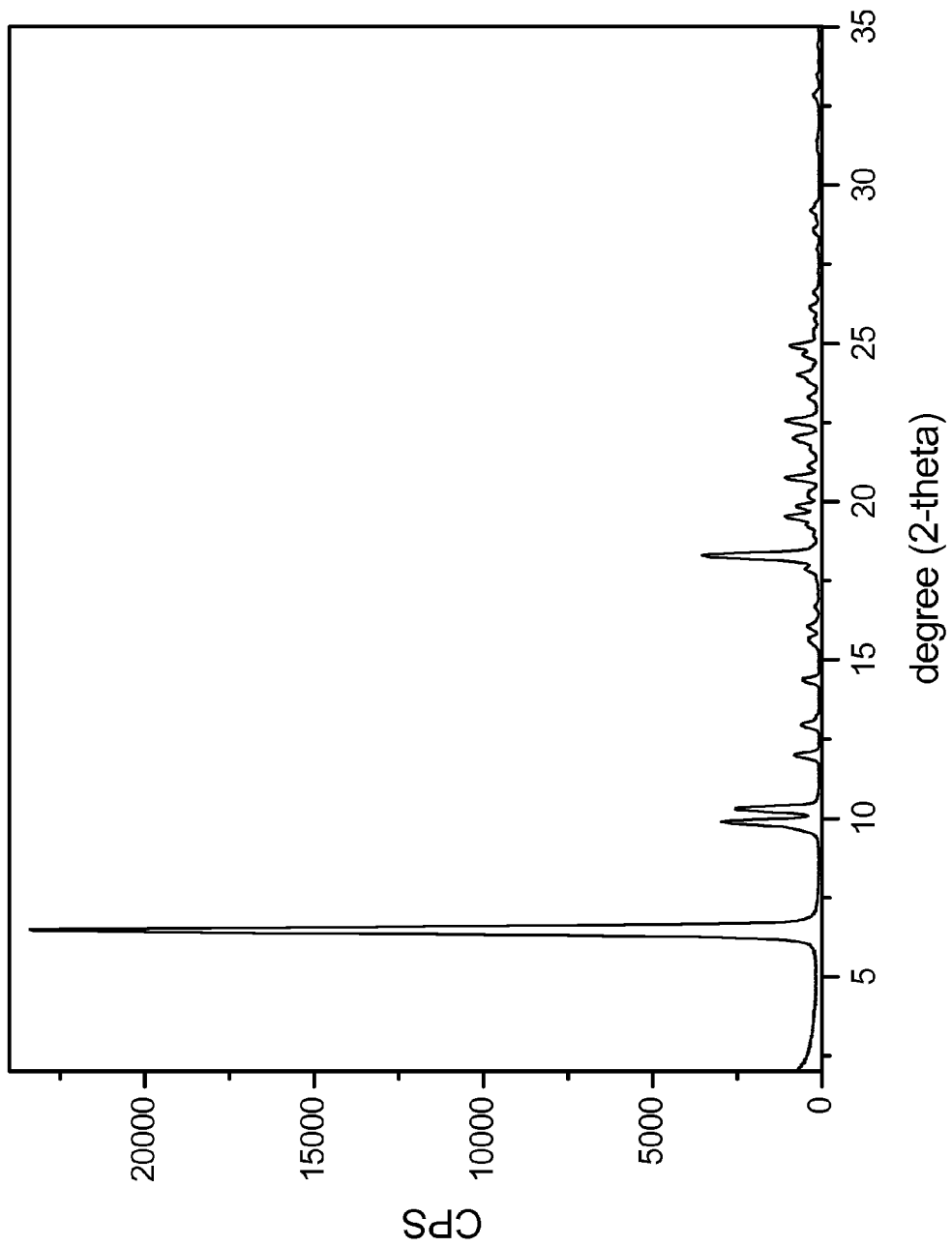
FIG. 2 shows the X-ray diffraction diagram of 5-(2,4-dihydroxy-5-isopropyl-phenyl)-4-(4-morpholin-4-ylmethyl-phenyl)-isoxazole-3-carboxylic acid ethylamide free base, form II.
Figure 3:
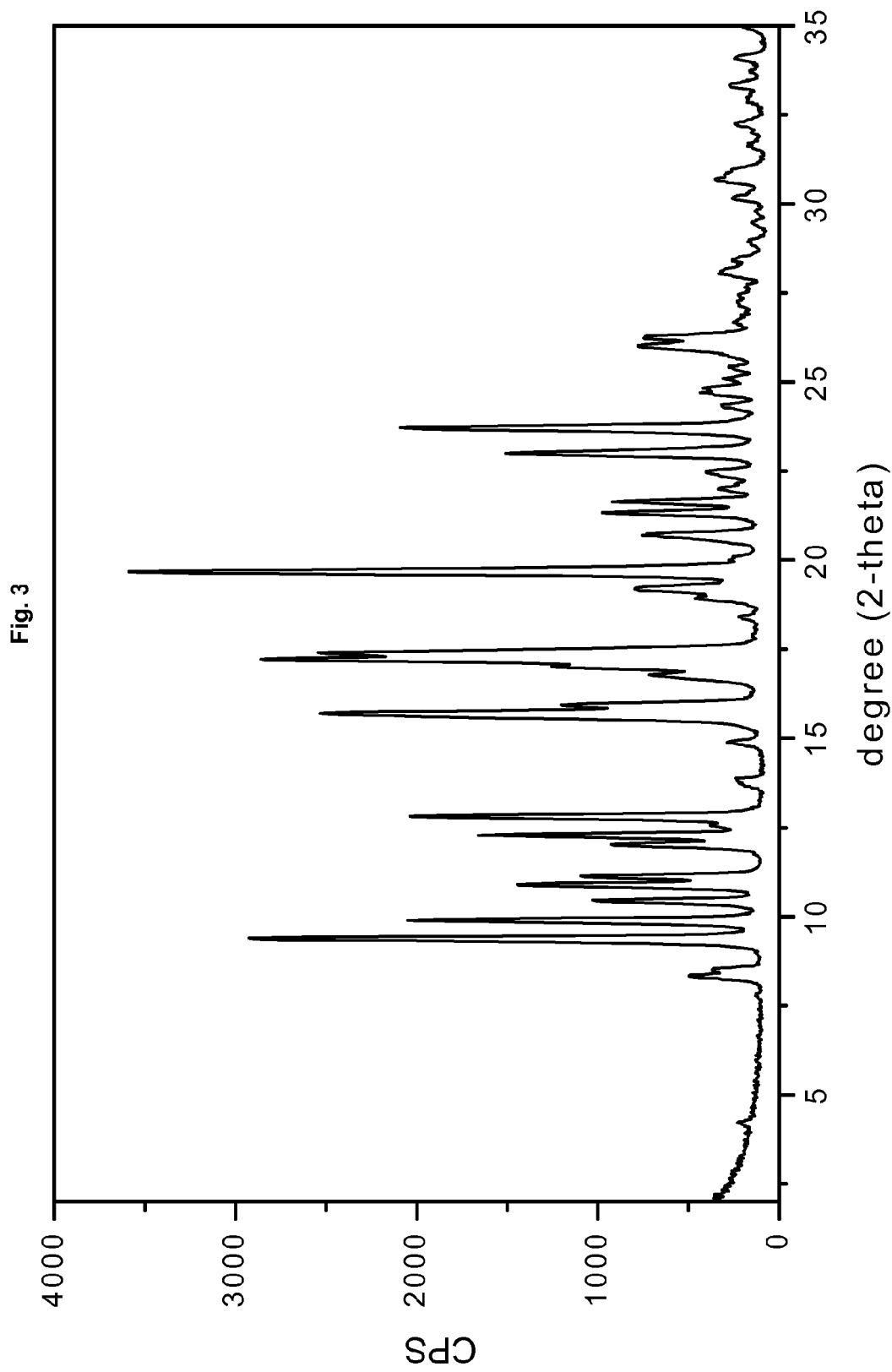
FIG. 3 shows the X-ray diffraction diagram of 5-(2,4-dihydroxy-5-isopropyl-phenyl)-4-(4-morpholin-4-ylmethyl-phenyl)-isoxazole-3-carboxylic acid ethylamide free base, form III.
Figure 4:
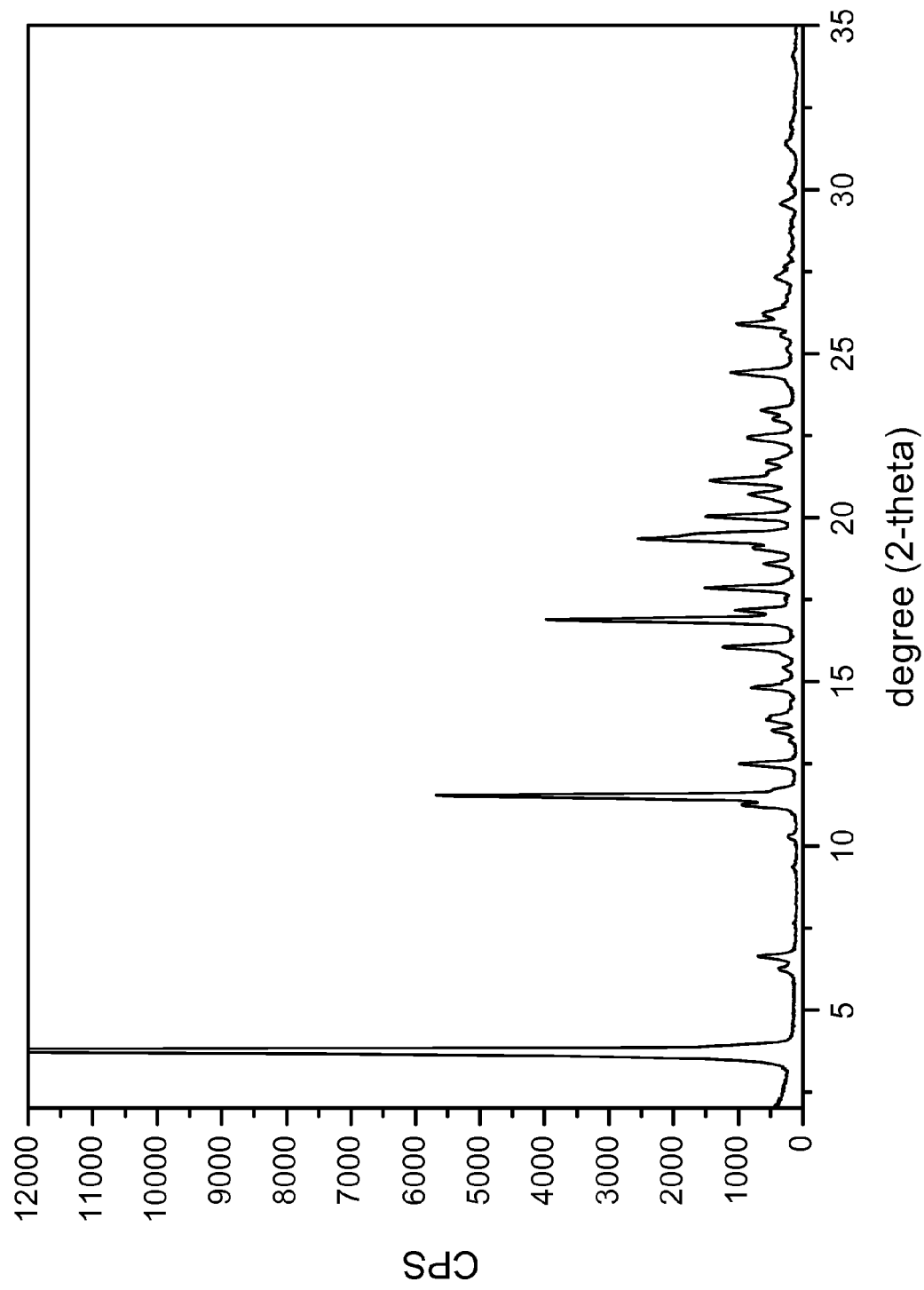
FIG. 4 shows the X-ray diffraction diagram of 5-(2,4-dihydroxy-5-isopropyl-phenyl)-4-(4-morpholin-4-ylmethyl-phenyl)-isoxazole-3-carboxylic acid ethylamide free base, form IV.
Figure 5:
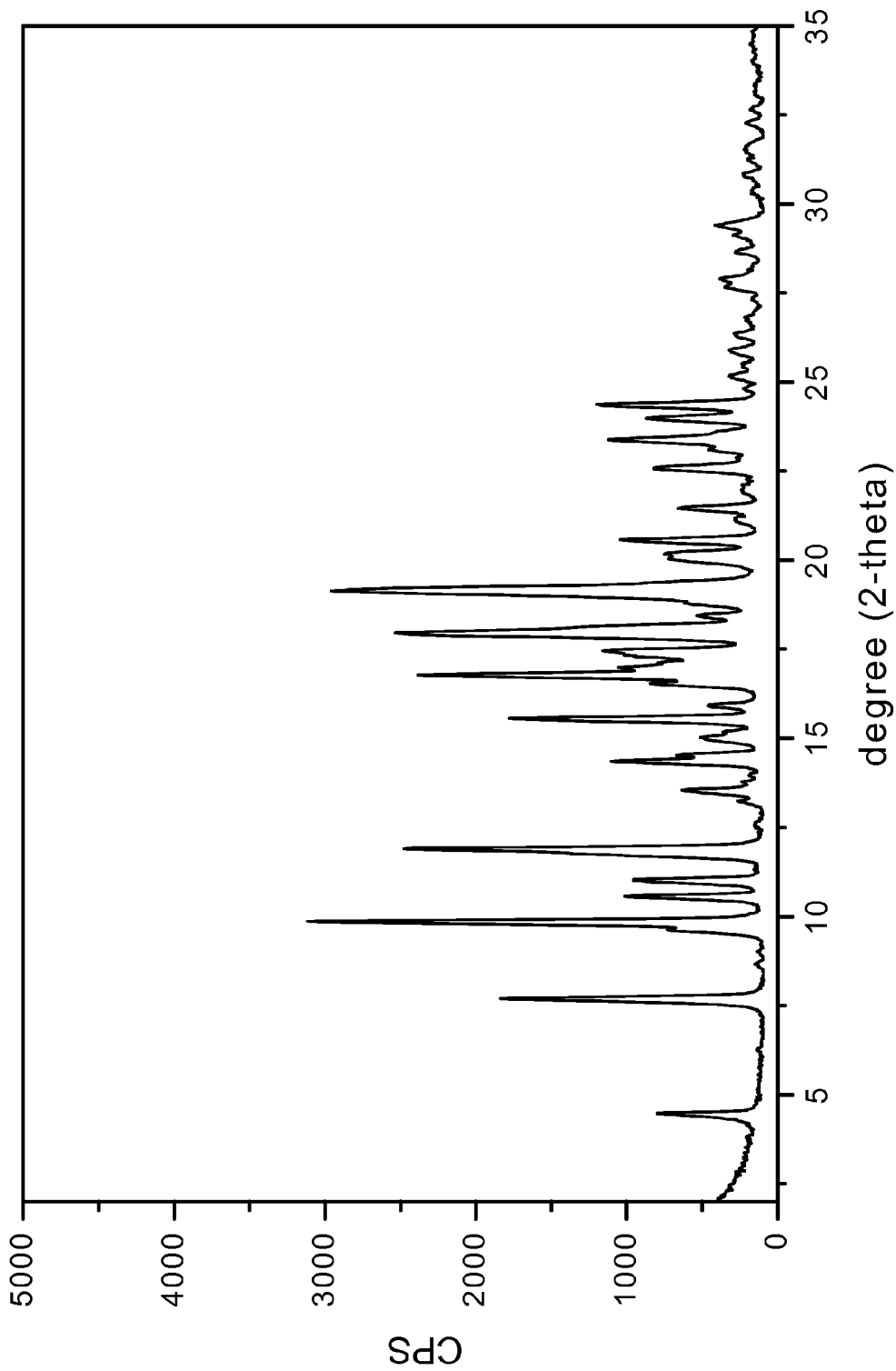
FIG. 5 shows the X-ray diffraction diagram of 5-(2,4-dihydroxy-5-isopropyl-phenyl)-4-(4-morpholin-4-ylmethyl-phenyl)-isoxazole-3-carboxylic acid ethylamide free base, form V.
Figure 6:
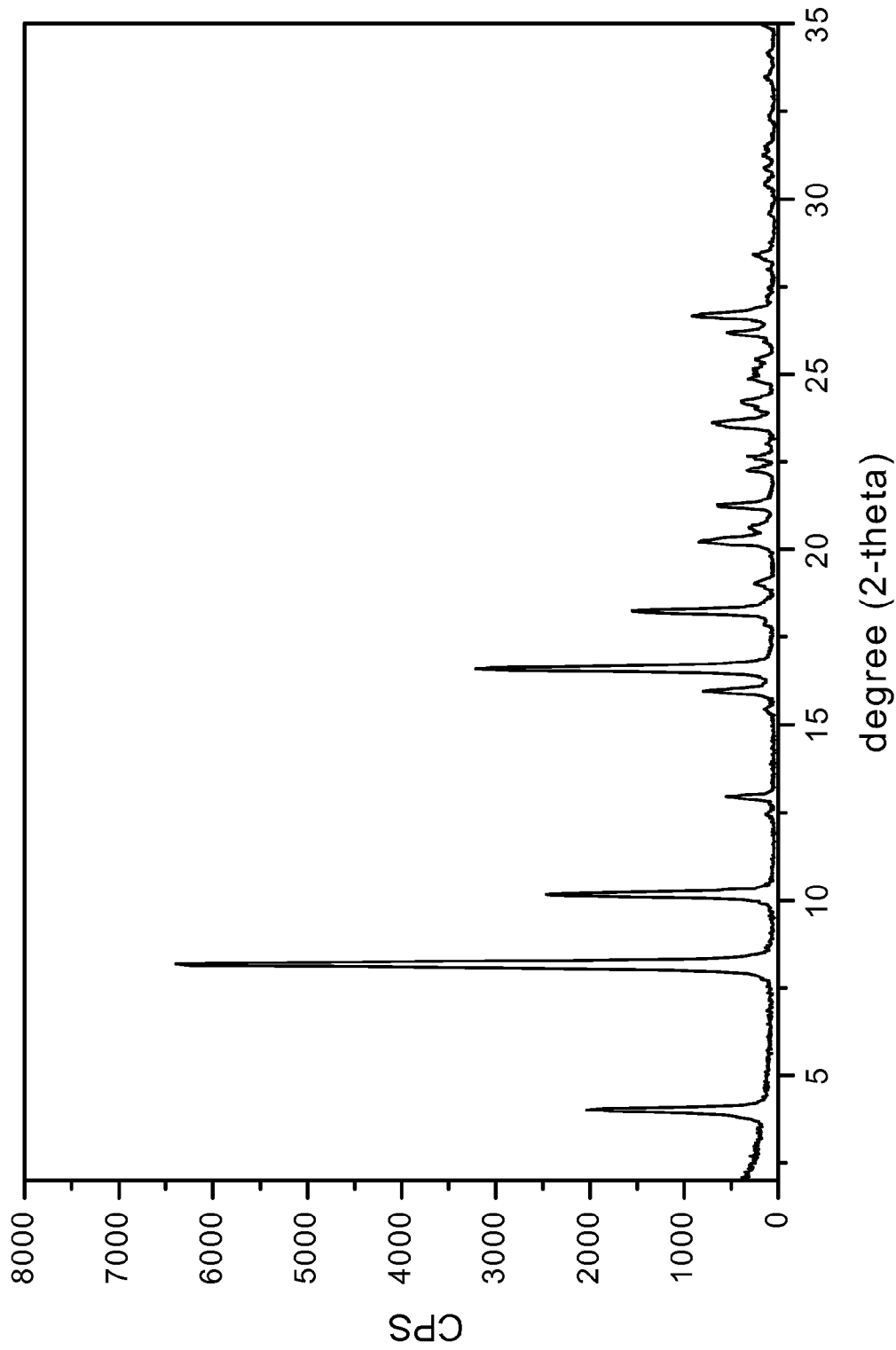
FIG. 6 shows the X-ray diffraction diagram of 5-(2,4-dihydroxy-5-isopropyl-phenyl)-4-(4-morpholin-4-ylmethyl-phenyl)-isoxazole-3-carboxylic acid ethylamide free base, form VII.
Figure 7:
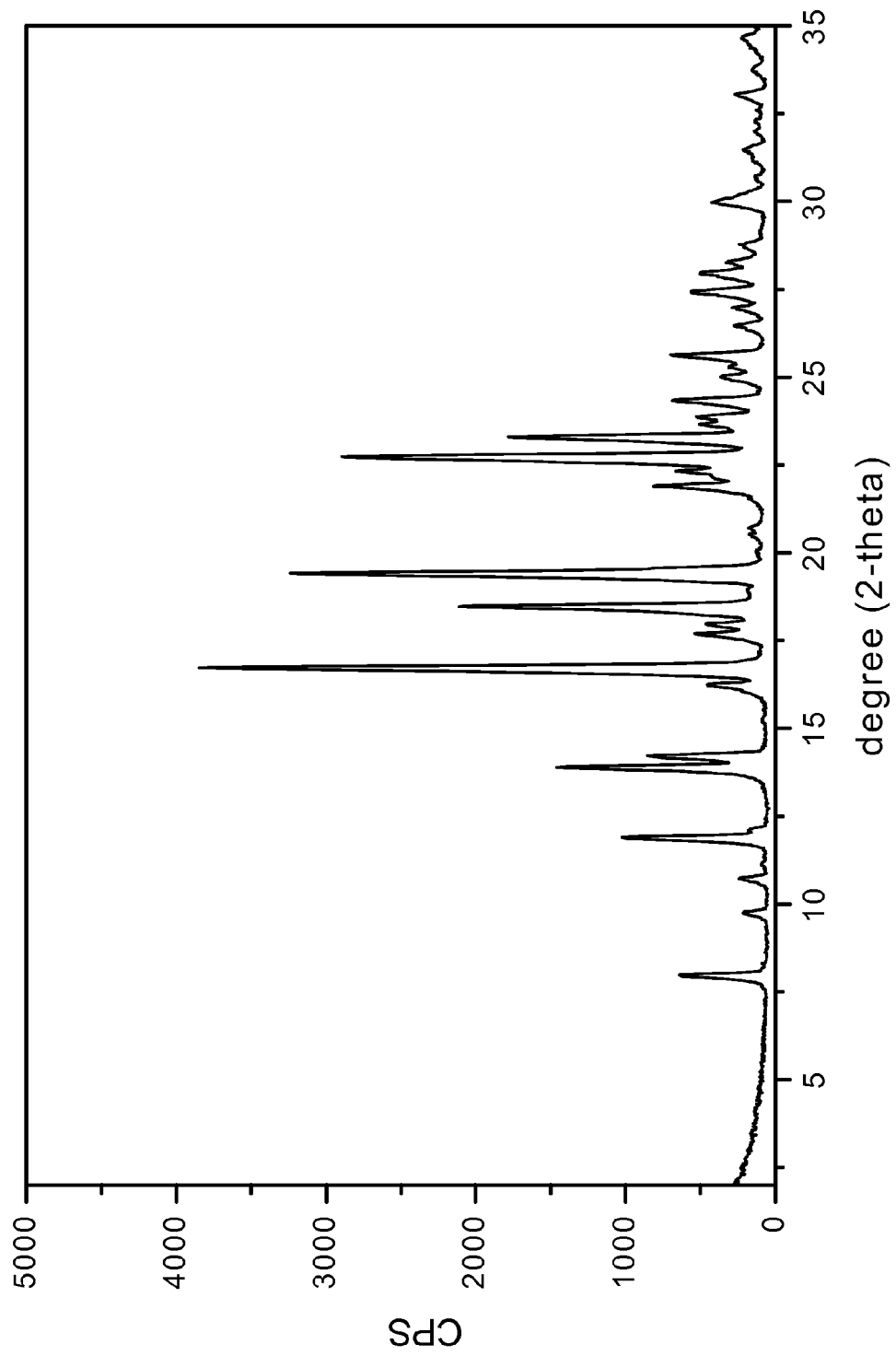
FIG. 7 shows the X-ray diffraction diagram of form I of the methane sulphonic acid salt of 5-(2,4-dihydroxy-5-isopropyl-phenyl)-4-(4-morpholin-4-ylmethyl-phenyl)-isoxazole-3-carboxylic acid ethylamide.

In a preferred embodiment, the form I of the essentially pure methane sulphonic acid salt of 5-(2,4-dihydroxy-5-isopropyl-phenyl)-4-(4-morpholin-4-ylmethyl-phenyl)-isoxazole-3-carboxylic acid ethylamide shows the X-ray diffraction diagram indicated in FIG. 7.

High preference is also given for the form I of the methane sulphonic acid salt of 5-(2,4-dihydroxy-5-isopropyl-phenyl)-4-(4-morpholin-4-ylmethyl-phenyl)-isoxazole-3-carboxylic acid ethylamide which shows an X-ray diffraction diagram of the type shown in FIG. 7, with significant peak intensities at 2-theta values: 16.7, 19.4 and 22.7±0.2 deg. In samples being free of any additional materials (other crystal forms, hydrates, excepients), it should be possible to observe the following 2-theta values: 8.0, 11.9, 13.9, 14.2, 16.7, 18.5, 19.4, 22.7, 23.3±0.2 deg.

Figure 8:
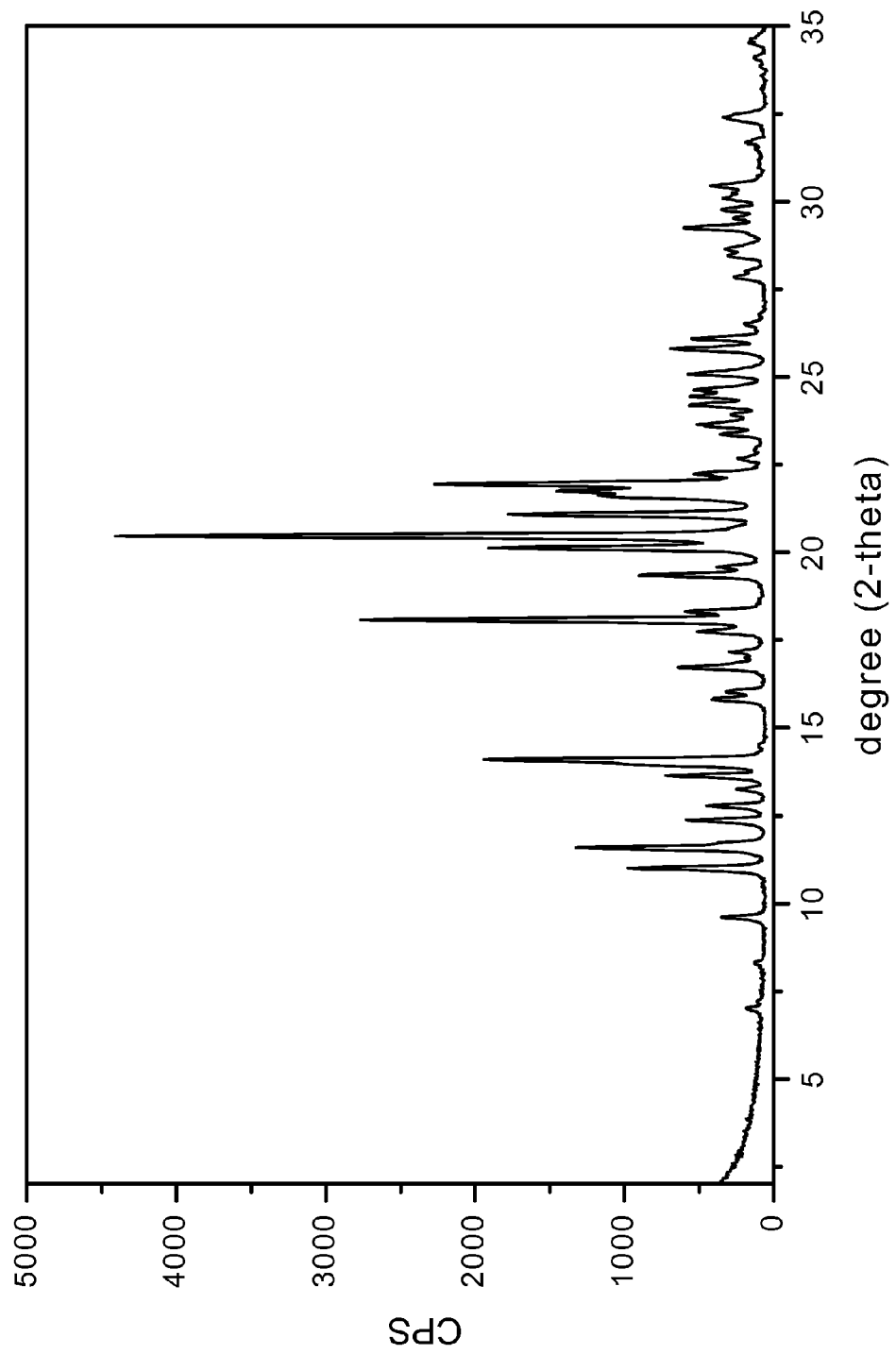
FIG. 8 shows the X-ray diffraction diagram of hydrate form $H_A$ of methane sulphonic acid salt of 5-(2,4-dihydroxy-5-isopropyl-phenyl)-4-(4-morpholin-4-ylmethyl-phenyl)-isoxazole-3-carboxylic acid ethylamide.

In another preferred embodiment, the form $H_A$ of the essentially pure methane sulphonic acid salt of 5-(2,4-dihydroxy-5-isopropyl-phenyl)-4-(4-morpholin-4-ylmethyl-phenyl)-isoxazole-3-carboxylic acid ethylamide shows the X-ray diffraction diagram indicated in FIG. 8.

High preference is also given for the form $H_A$ of the methane sulphonic acid salt of 5-(2,4-dihydroxy-5-isopropyl-phenyl)-4-(4-morpholin-4-ylmethyl-phenyl)-isoxazole-3-carboxylic acid ethylamide which shows an X-ray diffraction diagram of the type shown in FIG. 8, with significant peak intensities at 2-theta values: 18.1 and 20.5, ±0.2 deg. In samples being free of any additional materials (other crystal forms, anhydrate, excepients), it should be possible to observe the following 2-theta values: 11.0, 11.6, 14.1, 18.1, 20.1, 20.5, 21.1, 21.7, 21.9, 25.8±0.2 deg.

Figure 9:
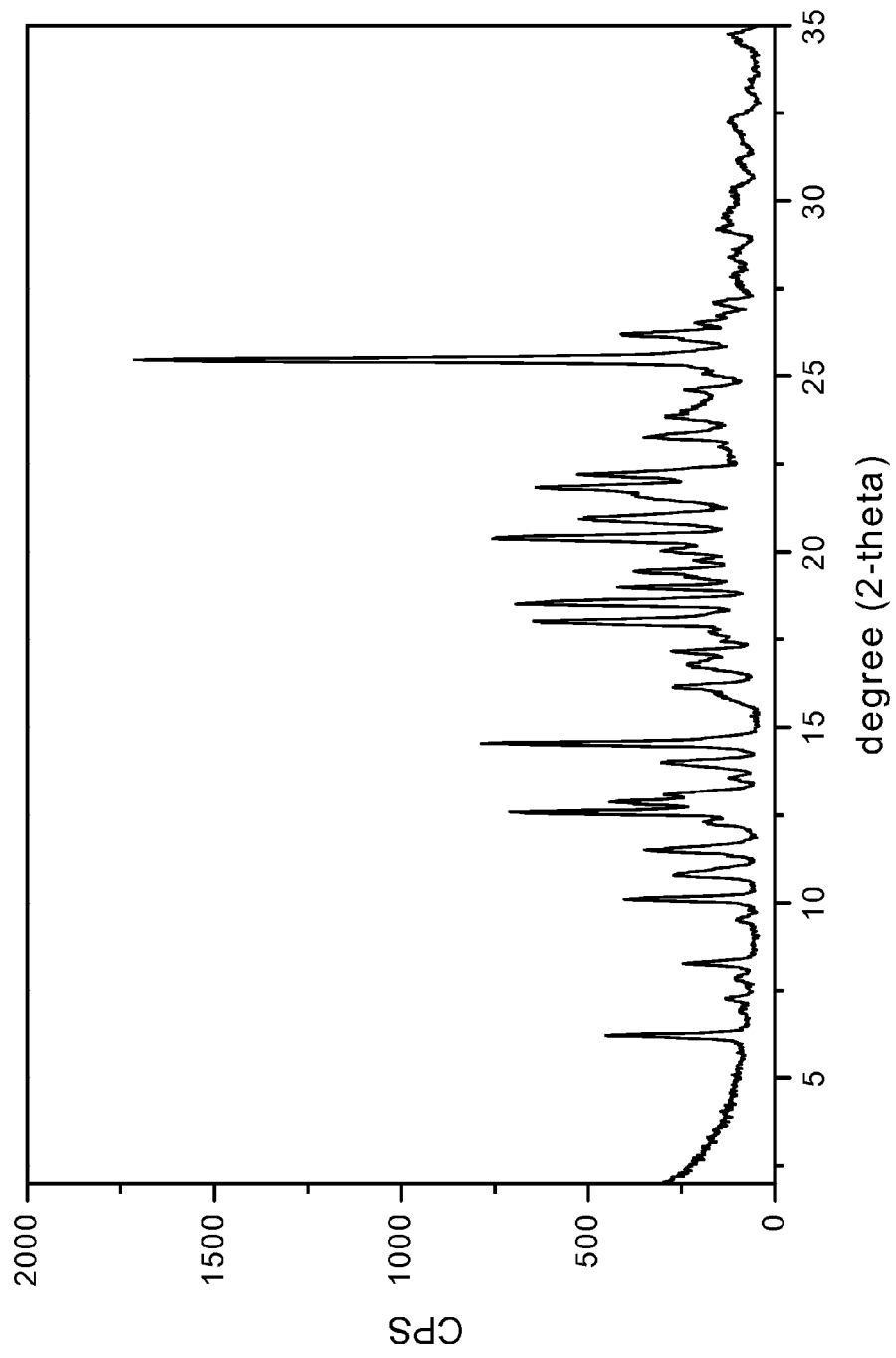
FIG. 9 shows the X-ray diffraction diagram of hydrate form $H_B$ of methane sulphonic acid salt of 5-(2,4-dihydroxy-5-isopropyl-phenyl)-4-(4-morpholin-4-ylmethyl-phenyl)-isoxazole-3-carboxylic acid ethylamide.

In a other preferred embodiment, the form $H_B$ of the essentially pure methane sulphonic acid salt of 5-(2,4-dihydroxy-5-isopropyl-phenyl)-4-(4-morpholin-4-ylmethyl-phenyl)-isoxazole-3-carboxylic acid ethylamide shows the X-ray diffraction diagram indicated in FIG. 9.

High preference is also given for the form $H_B$ of the methane sulphonic acid salt of 5-(2,4-dihydroxy-5-isopropyl-phenyl)-4-(4-morpholin-4-ylmethyl-phenyl)-isoxazole-3-carboxylic acid ethylamide which shows an X-ray diffraction diagram of the type shown in FIG. 9, with significant peak intensity at the 2-theta value of 25.4±0.2 deg. In samples being free of any additional materials (other crystal forms, anhydrate, excepients), it should be possible to observe the following 2-theta values: 6.2, 10.1, 12.6, 14.5, 18.0, 18.5, 19.0, 20.4, 20.9, 21.8, 22.2, 25.4±0.2 deg.

Figure 10:
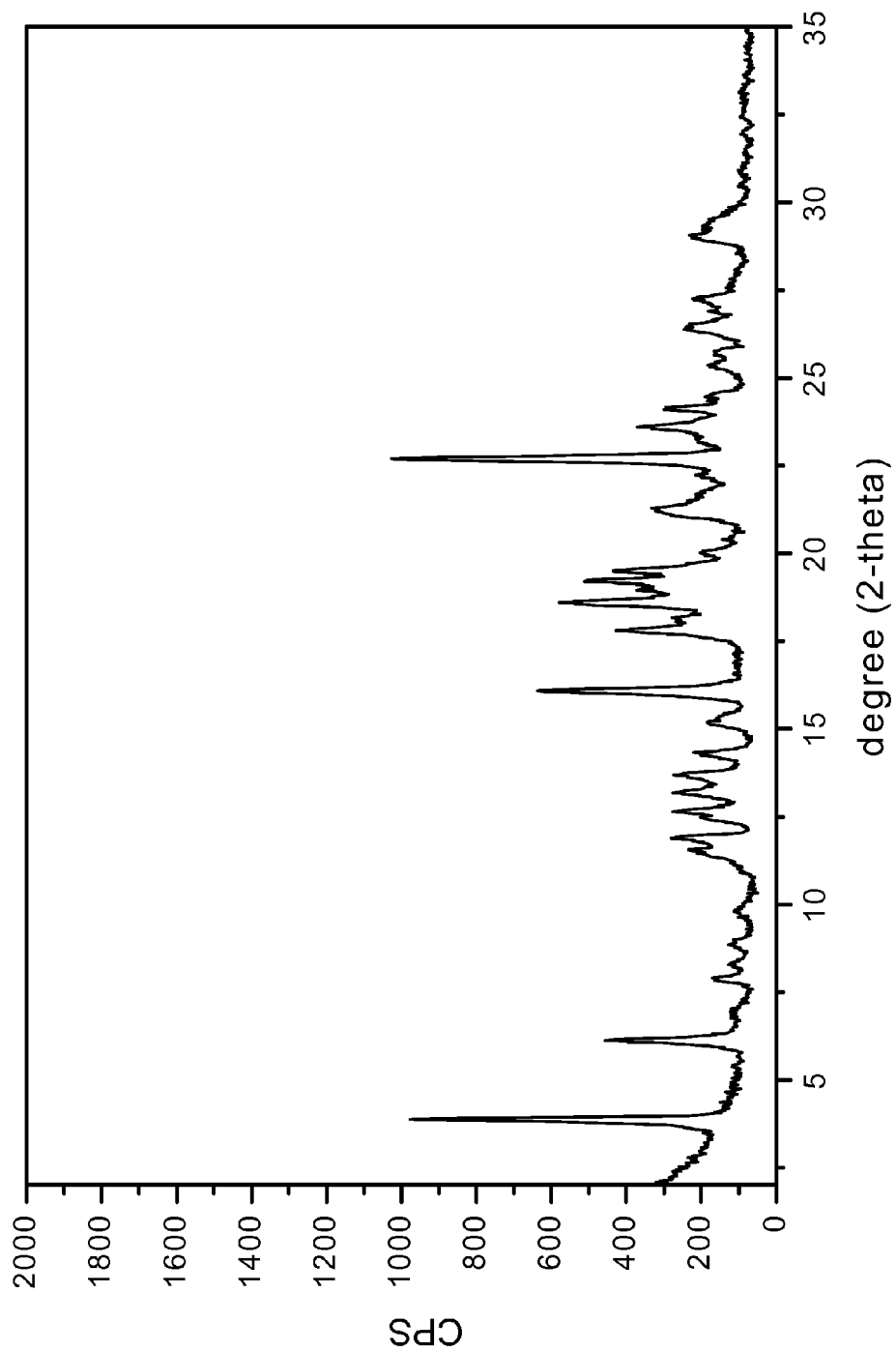
FIG. 10 shows the X-ray diffraction diagram of the hydrochloric salt of 5-(2,4-dihydroxy-5-isopropyl-phenyl)-4-(4-morpholin-4-ylmethyl-phenyl)-isoxazole-3-carboxylic acid ethylamide.

In another preferred embodiment, the essentially pure hydrochloric salt of 5-(2,4-dihydroxy-5-isopropyl-phenyl)-4-(4-morpholin-4-ylmethyl-phenyl)-isoxazole-3-carboxylic acid ethylamide shows the X-ray diffraction diagram indicated in FIG. 10.

High preference is also given for the hydrochloric salt of 5-(2,4-dihydroxy-5-isopropyl-phenyl)-4-(4-morpholin-4-ylmethyl-phenyl)-isoxazole-3-carboxylic acid ethylamide which shows an X-ray diffraction diagram of the type shown in FIG. 10.

Figure 11:
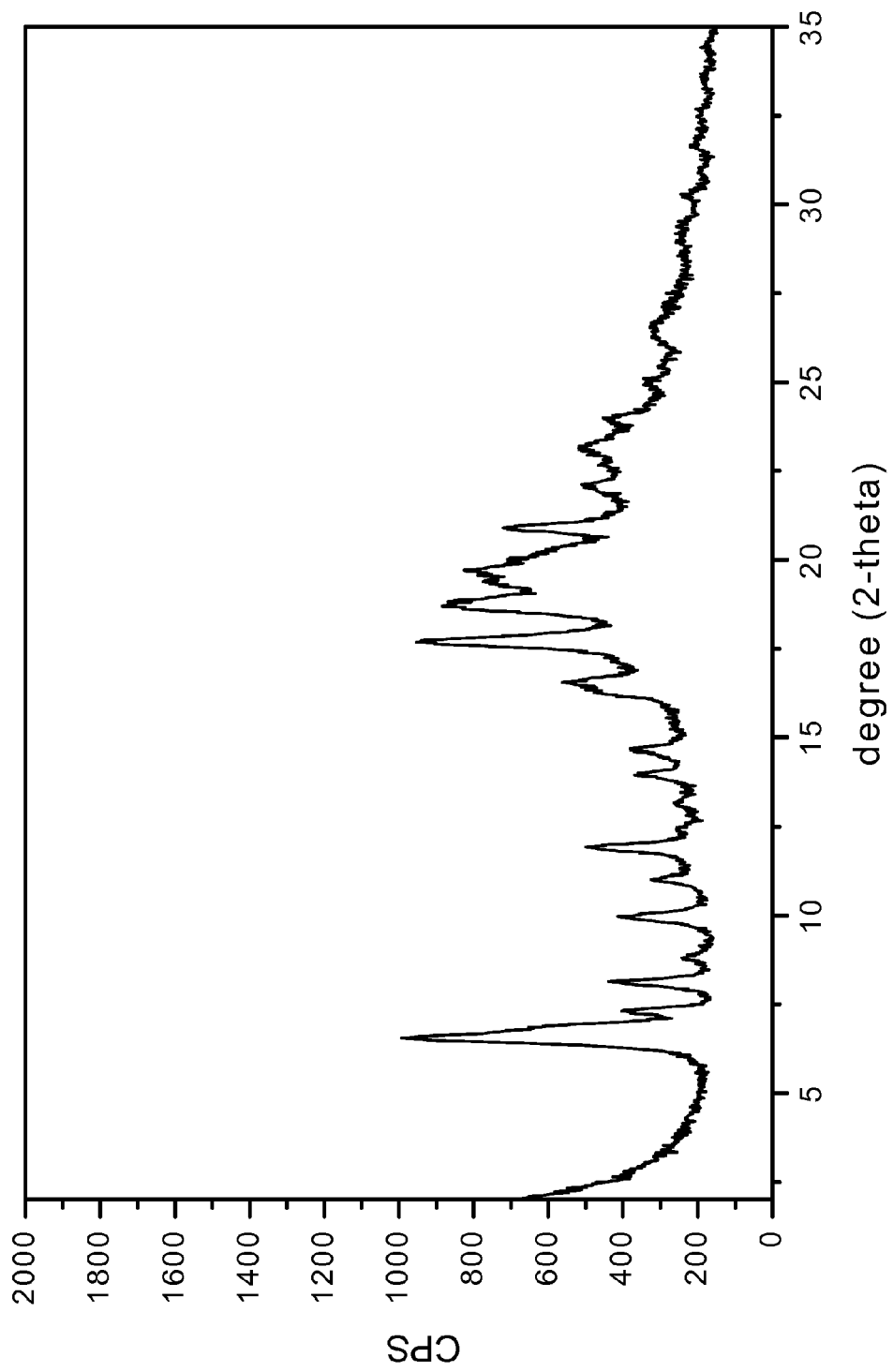
FIG. 11 shows the X-ray diffraction diagram of the tartaric acid salt of 5-(2,4-dihydroxy-5-isopropyl-phenyl)-4-(4-morpholin-4-ylmethyl-phenyl)-isoxazole-3-carboxylic acid ethylamide.

In another preferred embodiment, the essentially pure tataric acid salt of 5-(2,4-dihydroxy-5-isopropyl-phenyl)-4-(4-morpholin-4-ylmethyl-phenyl)-isoxazole-3-carboxylic acid ethylamide shows the X-ray diffraction diagram indicated in FIG. 11.

High preference is also given for the tataric acid salt of 5-(2,4-dihydroxy-5-isopropyl-phenyl)-4-(4-morpholin-4-ylmethyl-phenyl)-isoxazole-3-carboxylic acid ethylamide which shows an X-ray diffraction diagram of the type shown in FIG. 11.

Figure 12:
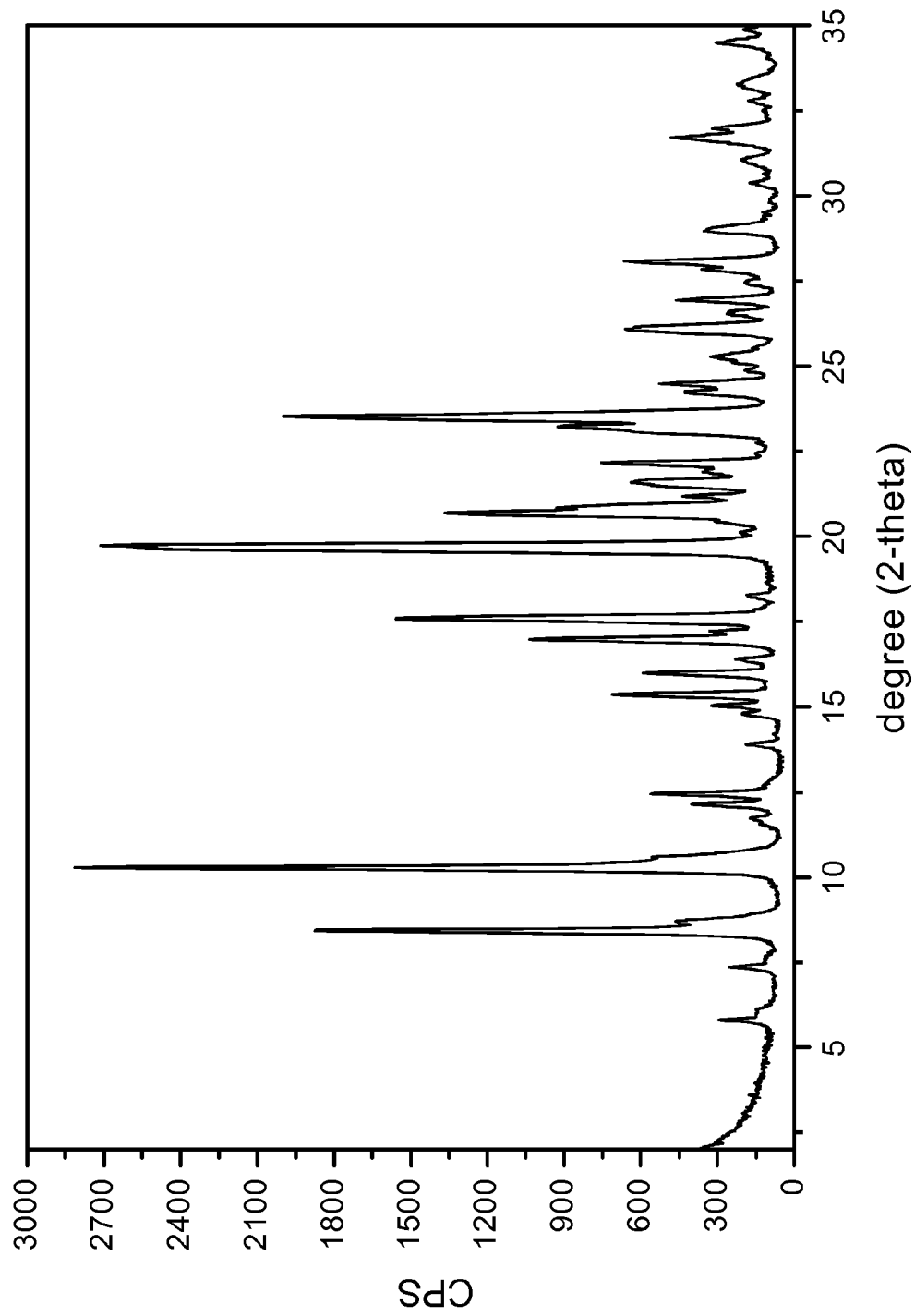
FIG. 12 shows the X-ray diffraction diagram of the phosphoric acid salt of 5-(2,4-dihydroxy-5-isopropyl-phenyl)-4-(4-morpholin-4-ylmethyl-phenyl)-isoxazole-3-carboxylic acid ethylamide.

In another preferred embodiment, the essentially pure phosphoric acid salt of 5-(2,4-dihydroxy-5-isopropyl-phenyl)-4-(4-morpholin-4-ylmethyl-phenyl)-isoxazole-3-carboxylic acid ethylamide shows the X-ray diffraction diagram indicated in FIG. 12.

High preference is also given for the phosphoric acid salt of 5-(2,4-dihydroxy-5-isopropyl-phenyl)-4-(4-morpholin-4-ylmethyl-phenyl)-isoxazole-3-carboxylic acid ethylamide which shows an X-ray diffraction diagram of the type shown in FIG. 12.

Figure 13:
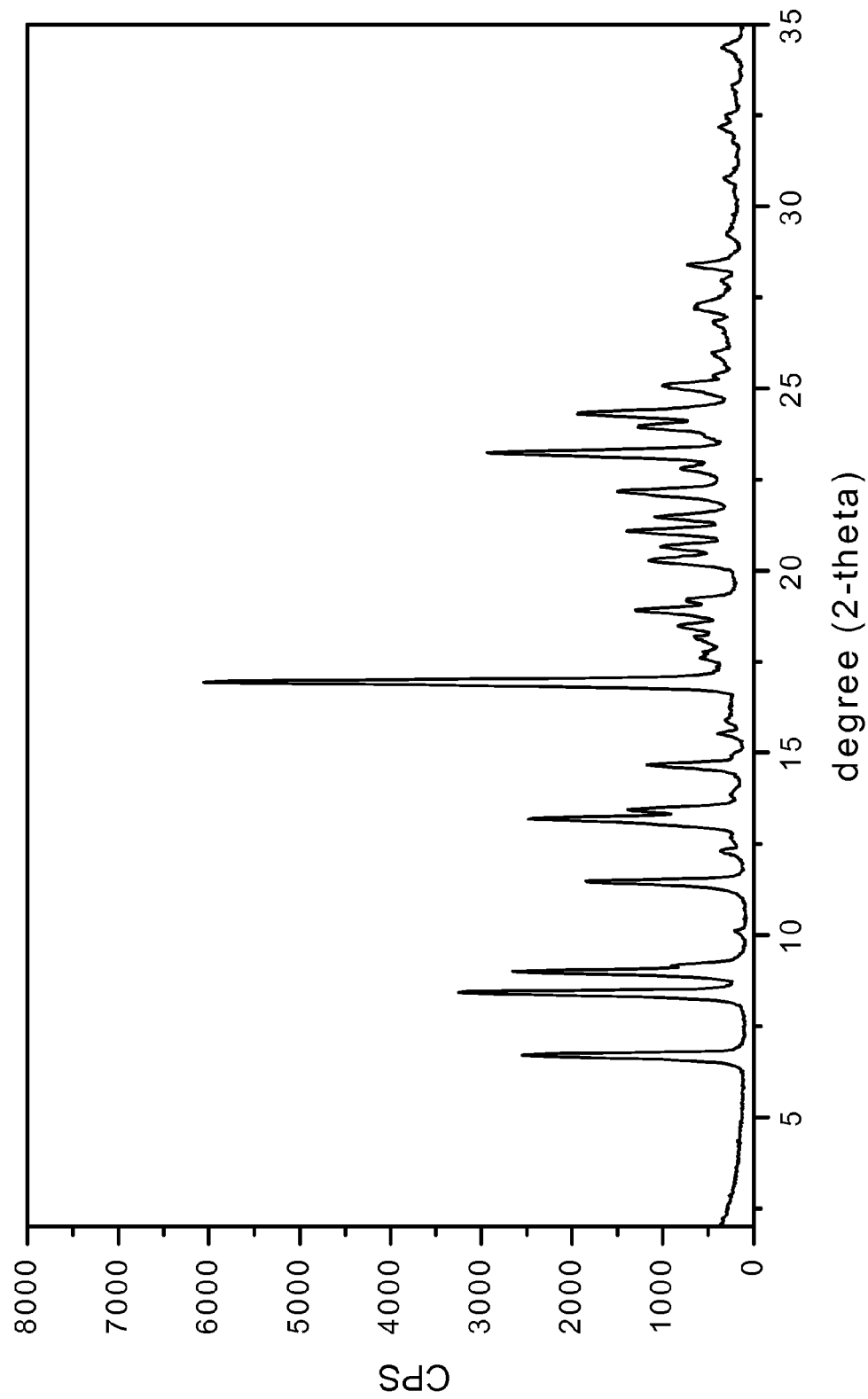
FIG. 13 shows the X-ray diffraction diagram of the hemi fumaric acid salt of 5-(2,4-dihydroxy-5-isopropyl-phenyl)-4-(4-morpholin-4-ylmethyl-phenyl)-isoxazole-3-carboxylic acid ethylamide.

In another preferred embodiment, the essentially pure fumaric acid salt of 5-(2,4-dihydroxy-5-isopropyl-phenyl)-4-(4-morpholin-4-ylmethyl-phenyl)-isoxazole-3-carboxylic acid ethylamide shows the X-ray diffraction diagram indicated in FIG. 13.

High preference is also given for the fumaric acid salt of 5-(2,4-dihydroxy-5-isopropyl-phenyl)-4-(4-morpholin-4-ylmethyl-phenyl)-isoxazole-3-carboxylic acid ethylamide which shows an X-ray diffraction diagram of the type shown in FIG. 13.

The term "essentially pure" is understood in the context of the present invention to mean especially that at least 90, preferably at least 95, and most preferably at least 99 percent by weight of the crystals of an acid addition salt of 5-(2,4-dihydroxy-5-isopropyl-phenyl)-4-(4-morpholin-4-ylmethyl-phenyl)-isoxazole-3-carboxylic acid ethylamide are present in the crystal form according to the invention.

In a further aspect the present invention provides a new formulation comprising 5-(2,4-dihydroxy-5-isopropyl-phenyl)-4-(4-morpholin-4-ylmethyl-phenyl)-isoxazole-3-carboxylic acid ethylamide mesylate. More specifically, the present invention provides an aqueous solution comprising 5-(2,4-dihydroxy-5-isopropyl-phenyl)-4-(4-morpholin-4-ylmethyl-phenyl)-isoxazole-3-carboxylic acid ethylamide mesylate being free of any other salts. Preferably, the aqueous solution has a pH between 3.2 and 5.2.

Preferably, the formulation comprises between around 4.8 and 5.2 mg/ml solution, more preferably 5.0 mg/ml solution, of 5-(2,4-dihydroxy-5-isopropyl-phenyl)-4-(4-morpholin-4-ylmethyl-phenyl)-isoxazole-3-carboxylic acid ethylamide mesylate. The pH of such a solution is around 4.2 and therefore at the stability maximum of the mesylate salt. This surprising finding renders the solution particularly suitable for pharmaceutical use. In particular, it allows to use the solution without any other excipients, such as buffers, for stabilizing the drug substance. Furthermore, in view of its high stability the solution comprising between around 4.8 and 5.2 mg/ml solution of 5-(2,4-dihydroxy-5-isopropyl-phenyl)-4-(4-morpholin-4-ylmethyl-phenyl)-isoxazole-3-carboxylic acid ethylamide mesylate can be subjected to autoclavation (e.g. by heating to about 120° C., for 20 to 40 minutes, e.g. 30 minutes, under a pressure of around 2 bar) without causing any color changes or degradation products.

In one embodiment, the formulation consists of the mesylate salt of an isotonic aqueous solution of 5-(2,4-dihydroxy-5-isopropyl-phenyl)-4-(4-morpholin-4-ylmethyl-phenyl)-isoxazole-3-carboxylic acid ethylamide and 5% w/w of glucose or mannitol. The latter embodiment has the further advantage that crystal formation can be avoided even after longer storage time, e.g. several months. Furthermore, the mesylate salt is chemically stable in this formulation. Furthermore, the pH of such a solution prevents Maillard reactions during autoclavation of the 5% glucose solution which would lead to discoloration at neutral pH.

In view of the surprising findings listed above, the present invention provides a formulation comprising 5-(2,4-dihydroxy-5-isopropyl-phenyl)-4-(4-morpholin-4-ylmethyl-phenyl)-isoxazole-3-carboxylic acid ethylamide mesylate, which is preferably an aqueous solution comprising 5-(2,4-dihydroxy-5-isopropyl-phenyl)-4-(4-morpholin-4-ylmethyl-phenyl)-isoxazole-3-carboxylic acid ethylamide mesylate being free of any other salts, having preferably a pH between 3.2 and 5.2;

in particular a formulation consisting of an isotonic aqueous solution of the mesylate salt of 5-(2,4-dihydroxy-5-isopropyl-phenyl)-4-(4-morpholin-4-ylmethyl-phenyl)-isoxazole-3-carboxylic acid ethylamide and 5% w/w of glucose or mannitol;

and in particular an aqueous formulation comprising 5-(2,4-dihydroxy-5-isopropyl-phenyl)-4-(4-morpholin-4-ylmethyl-phenyl)-isoxazole-3-carboxylic acid ethylamide mesylate in a concentration between around 4.8 and 5.2 mg/ml.

The aqueous solution described herein above is particularly useful for intravenous administration of 5-(2,4-dihydroxy-5-isopropyl-phenyl)-4-(4-morpholin-4-ylmethyl-phenyl)-isoxazole-3-carboxylic acid ethylamide mesylate.

Furthermore, it was surprisingly found that 5-(2,4-dihydroxy-5-isopropyl-phenyl)-4-(4-morpholin-4-ylmethyl-phenyl)-isoxazole-3-carboxylic acid ethylamide mesylate is light sensitive as solid as well as in solution. Hence, in a further embodiment, the present invention provides for amber glass containers being filled with the drug substance or the aqueous formulations described herein above.

Furthermore, the present invention provides for a method for treating a disorder mediated by Hsp90 comprising administering to a warm-blooded animal in need thereof a therapeutically active amount of 5-(2,4-dihydroxy-5-isopropyl-phenyl)-4-(4-morpholin-4-ylmethyl-phenyl)-isoxazole-3-carboxylic acid ethylamide mesylate or 5-(2,4-dihydroxy-5-isopropyl-phenyl)-4-(4-morpholin-4-ylmethyl-phenyl)-isoxazole-3-carboxylic acid ethylamide hydrochloride.

EXAMPLES

The following Examples illustrate the invention.

Temperatures are measured in degrees Celsius (° C.). Unless otherwise indicated, the reactions take place at room temperature.

ABBREVIATIONS

EtOAc ethyl acetate
r.h. relative humidity
RT room temperature
TBME tert-butyl methyl ether

Example 1

5-(2,4-Dihydroxy-5-isopropyl-phenyl)-4-(4-morpholin-4-ylmethyl-phenyl)-isoxazole-3-carboxylic acid ethylamide hydrochloric acid salt

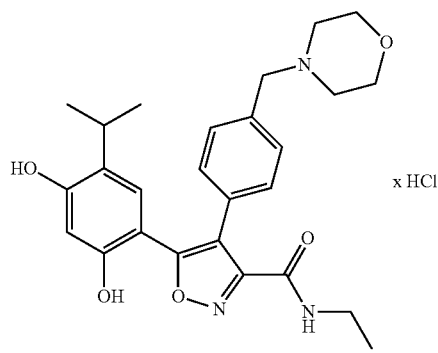 [SMILES: CCNC(=O)c1noc(-c2cc(C(C)C)c(O)cc2O)c1-c1ccc(CN2CCOCC2)cc1]

5-(2,4-Dihydroxy-5-isopropyl-phenyl)-4-(4-morpholin-4-ylmethyl-phenyl)-isoxazole-3-carboxylic acid ethylamide (4.19 g, 9 mmol) is dissolved in absolute alcohol (19.7 ml) under gentle warming. After stirring for 5 min, 6N aqueous hydrochloric acid (1.5 ml, 9 mmol) is added at RT (about 25° C.). The clear solution is seeded with a very small amount of 5-(2,4-dihydroxy-5-isopropyl-phenyl)-4-(4-morpholin-4-ylmethyl-phenyl)-isoxazole-3-carboxylic acid ethylamide hydrochloric acid salt and ethyl acetate (2 ml) is added whereupon the mixture becomes turbid slowly. After 1 h EtOAc (5 ml) is added in portions, and the suspension is stirred at RT overnight. More EtOAc (2 ml) is added. The suspension is stirred for about 5 h and filtered. The filter cake is washed with absolute alcohol/EtOAc 1:1 (v/v) and dried for 16 h at 45° C. under reduced pressure to result in the title compound as a white powder.

Melting point (DSC): 237° C.

Example 2

5-(2,4-Dihydroxy-5-isopropyl-phenyl)-4-(4-morpholin-4-ylmethyl-phenyl)-isoxazole-3-carboxylic acid ethylamide mesylate—Conditions (A)

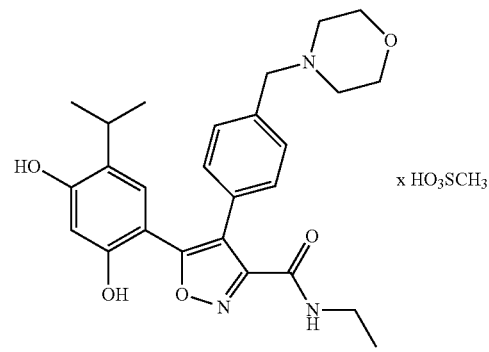 [SMILES: CCNC(=O)c1noc(-c2cc(C(C)C)c(O)cc2O)c1-c1ccc(CN2CCOCC2)cc1]

A stirred suspension of 5-(2,4-dihydroxy-5-isopropyl-phenyl)-4-(4-morpholin-4-ylmethyl-phenyl)-isoxazole-3-carboxylic acid ethylamide (7.76 g, 15 mmol, containing about 9 wt % TBME) in acetone (15 ml) is warmed to 35° C. To the mixture is added a solution of methanesulfonic acid (1.43 g, 14.85 mmol) in water (3.33 g) over 20 min. After 15 min, the solution is warmed to 45° C. and clear filtered into a warm flask (about 45° C.). The filter is rinsed with acetone/water 9:1 (v/v, 12 ml). The 45° C. warm filtrate is diluted with acetone (53 ml) over 30 min and seeded with 5-(2,4-dihydroxy-5-isopropyl-phenyl)-4-(4-morpholin-4-ylmethyl-phenyl)-isoxazole-3-carboxylic acid ethylamide methanesulfonic acid salt (4 mg) whereupon crystallization begins. After 1 h at 45° C. acetone (30 ml) is added. The suspension is stirred at 45° C. for 1 h before it is cooled to 24° C. over 90 min. TBME (20 ml) is added, and the suspension is stirred at about 24° C. for 15 h. Two more portions of TBME (20 ml each) are added followed by 2 h stirring each time. Thereafter, the suspension is cooled to 0-5° C. and stirred for 3 h before it is filtered. The filter cake is washed with acetone/tert-butyl methyl ether 3:1 (v/v) and dried under reduced pressure at 50° C. for about 17 h to give 7.18 g (85%) of the title compound as a white, crystalline powder.

Melting point: 233° C.

When seeding is left out, the formed crystals are of the same form but may contain up to 1.5 wt % of acetone.

Example 3

5-(2,4-Dihydroxy-5-isopropyl-phenyl)-4-(4-morpholin-4-ylmethyl-phenyl)-isoxazole-3-carboxylic acid ethylamide mesylate—Conditions (B)

186.2 mg (0.4 mmol) of 5-(2,4-Dihydroxy-5-isopropyl-phenyl)-4-(4-morpholin-4-ylmethyl-phenyl)-isoxazole-3-carboxylic acid ethylamide methane sulphonic acid are dissolved in 0.75 ml acetone. 154 mg of an aqueous solution (25% w/w) of methane sulphonic acid (0.4 mmol) are added at RT resulting in a blue solution. After stirring for 2 h, 3.5 ml acetone and 0.5 ml TBME are added. After the solution is stirred for further 12 h, further 3.5 ml of TBME is slowly added, and stirring is continued for further 12 h. The obtained emulsion is filtrated and the obtained solid washed with 0.5 ml TBME. The solid is dried for 16 h at 50° C. at 20 mbar to provide 180 mg of the title compound.

Example 4

Hygroscopicity of the free base, the methane sulphonic acid salt and the hydrochloric salt of 5-(2,4-dihydroxy-5-isopropyl-phenyl)-4-(4-morpholin-4-ylmethyl-phenyl)-isoxazole-3-carboxylic acid ethylamide Hygroscopicity is measured using a Dynamic Water Sorption (DVS) apparatus. Measurements are performed at 25° C. using about 8-10 mg of substance. The r.h. is changed in steps of 10% r.h. as follows: 40-0-95-0-40% r.h. The minimum stage time is 60 min, the maximum 180 min, if the change in mass of 10 min is less than 0.002%/min, the r.h. is changed to the next step.

Neither of 5-(2,4-dihydroxy-5-isopropyl-phenyl)-4-(4-morpholin-4-ylmethyl-phenyl)-isoxazole-3-carboxylic acid ethylamide mesylate and 5-(2,4-dihydroxy-5-isopropyl-phenyl)-4-(4-morpholin-4-ylmethyl-phenyl)-isoxazole-3-carboxylic acid ethylamide hydrochloride was found to be hygroscopic. The free base is slightly hygroscopic showing a maximum uptake of 1.8% of water at 80% relative humidity (r.h.) at 25° C.

Example 5

Manufacturing of 50 mg/10 mL liquid in ampoule of 5-(2,4-dihydroxy-5-isopropyl-phenyl)-4-(4-morpholin-4-ylmethyl-phenyl)-isoxazole-3-carboxylic acid ethylamide mesylate 391.95 g of AUY922 mesylate salt (which corresponds to 325 g free base) and 3.25 kg glucose are dissolved in 65 L water for injection. A colorless to slightly yellowish solution is obtained with a density of 1.018±0.005 g/mL at 20° C., an osmolarity of 315±15 mOsm/kg and a pH of 4.2±1.0. The solution is filtered through 0.22 μm. 10.5±0.4 mL of the solution are filled into an amber glass ampoule. The ampoule are sealed under nitrogen atmosphere and autoclaved for 30 min at 121° C.

Example 6

Dilution of the 50 mg/10 mL concentrate of Example 5

10 mL of the 50 mg/10 mL ampoule of Example 5 are diluted with commercially available 250 mL 5% glucose solution and administered via a gravimetric infusion line intravenously to the patient.

Example 7

Solubility of 5-(2,4-dihydroxy-5-isopropyl-phenyl)-4-(4-morpholin-4-ylmethyl-phenyl)-isoxazole-3-carboxylic acid ethylamide mesylate The solubility of the 5-(2,4-dihydroxy-5-isopropyl-phenyl)-4-(4-morpholin-4-ylmethyl-phenyl)-isoxazole-3-carboxylic acid ethylamide (AUY922) mesylate salt in different aqueous media were determined and found to be as follows:

Water (pH of the saturated solution=3.6) 37.5 mg/mL; 0.9% NaCl solution 12.8 mg/mL; 5% glucose solution 39 mg/mL; 5% mannitol solution 39 mg/mL; 5% glucose solution pH 4 35.6 mg/mL; 5% glucose solution pH 7 37.5 mg/mL: Buffer solutions pH 4.0 (acetate buffer) 14.6 mg/mL; pH 5.0 (acetate buffer) 3.2 mg/mL; pH 6.0 (phosphate buffer) 0.6 mg/mL; pH 7.0 (phosphate buffer) 0.7 mg/mL; pH 8.0 (borate buffer) 1.8 mg/mL.

High solubilities were found in glucose and mannitol solutions. In buffered solutions a pH of 4 was leading to highest solubilities.

Example 8

Stress tests in solution or suspensions of 5-(2,4-dihydroxy-5-isopropyl-phenyl)-4-(4-morpholin-4-ylmethyl-phenyl)-isoxazole-3-carboxylic acid ethylamide mesylate The stability of the AUY922 mesylate salt in different aqueous media were determined under stress conditions (4 weeks at 50° C.) and the following appearance/content recovery/sum of by- and degradation products were found:

Water: colorless solution/97.0%/0.32%; 0.9% NaCl: solution colorless solution/98.5%/0.34%; 5% glucose solution: colorless solution/99.6%/0.34%.

Buffer solutions pH1.0 (HCl): colorless solution/96.7%/2.83%; pH2.0 (citrate buffer): colorless solution/97.8%/0.58%; pH3.0 (citrate buffer): colorless solution/99.2%/0.47%; pH 4.0 (acetate buffer): colorless solution/100.5%/0.36%; pH 5.0 (acetate buffer): colorless solution/99.1%/0.50%; pH 6.0 (phosphate buffer): colorless suspension/96.2%/0.49%; pH 6.8 (phosphate buffer): colorless suspension/96.3%/0.79%; pH8.0 (borate buffer): colorless suspension/88.5%/0.26%.

This data demonstrate the stability maximum of the AUY922 mesylate salt at pH 4. Further it was shown that 5% glucose solution resulted in max. stability compared to other aqueous media.

What is claimed is:

1. A salt which is 5-(2,4-dihydroxy-5-isopropyl-phenyl)-4-(4-morpholin-4-ylmethyl-phenyl)-isoxazole-3-carboxylic acid ethylamide hydrochloride or a hydrate thereof.

2. A crystalline form of the salt according to claim 1.

3. A crystalline form according to claim 2 which shows an X-ray diffraction diagram of the type shown in FIG. 10, in which the relative peak intensities of each peak do not deviate by more than 10% of the relative peak intensities in the diagram shown in FIG. 10.

* * * * *